United States Patent
Krahbichler et al.

[11] Patent Number: 6,062,218
[45] Date of Patent: May 16, 2000

[54] FLOW REGULATOR

[75] Inventors: Erik Krahbichler, Solna; Per-Göran Eriksson, Täby; Mikael Kock, Åkersberga; Jan Bolmgren, Vällingby, all of Sweden

[73] Assignee: Siemens-Elema AB, Solna, Sweden

[21] Appl. No.: 08/919,265

[22] Filed: Aug. 28, 1997

[30] Foreign Application Priority Data

Sep. 12, 1996 [SE] Sweden ............................ 9603313

[51] Int. Cl.$^7$ ............................................. A62B 9/02
[52] U.S. Cl. ................................. 128/205.24; 128/912
[58] Field of Search ................. 251/4, 9; 128/205.24, 128/912

[56] References Cited

U.S. PATENT DOCUMENTS

| | | | |
|---|---|---|---|
| 579,501 | 3/1897 | Smith et al. | 251/9 |
| 2,197,310 | 4/1940 | Lincoln | 251/9 |
| 2,572,658 | 10/1951 | Perkins | 251/4 |
| 3,411,534 | 11/1968 | Rose | 251/9 |
| 3,648,701 | 3/1972 | Botts | 251/9 |
| 4,073,467 | 2/1978 | Little et al. | 251/7 |
| 4,177,830 | 12/1979 | Munson | 128/205.24 |
| 4,259,985 | 4/1981 | Bergmann | 137/595 |
| 4,588,159 | 5/1986 | Kawai et al. | 251/4 |
| 4,682,755 | 7/1987 | Bernstein et al. | 251/4 |
| 5,078,361 | 1/1992 | Nordman | 251/7 |
| 5,083,561 | 1/1992 | Russo | 128/912 |
| 5,139,018 | 8/1992 | Brodsky et al. | 128/912 |
| 5,152,497 | 10/1992 | Bissell | 251/9 |
| 5,154,704 | 10/1992 | Archibald | 251/9 |
| 5,191,881 | 3/1993 | Beck | 128/205.24 |
| 5,230,497 | 7/1993 | Atkins | 251/9 |
| 5,413,566 | 5/1995 | Servain et al. | 604/248 |
| 5,490,536 | 2/1996 | Cole et al. | 251/4 |

OTHER PUBLICATIONS

Service Manual for Siemens Servo Ventilator 300 (1992), pp. 74–75.
Solenoids Design Manual, Shindengen Electric Mfg., Co., Ltd. (1995), pp. 1, 6–9, 11, 20–23.

*Primary Examiner*—Aaron J. Lewis
*Attorney, Agent, or Firm*—Hill & Simpson

[57] ABSTRACT

A flow regulator, preferably in a respirator/ventilator, has a conduit through which a medium conduit flow is to be regulated flows and a choker valve arranged outside the conduit, the choker valve having pressure applicators arranged exactly opposite one another between which the conduit can be brought and act on the flow cross-section of the conduit such that they leave the flow cross-section of the conduit uninfluenced in a first limit position and press the conduit completely closed in a second limit position. In order to obtain a flow regulator of this type with a choker valve that is gentle on the conduit and which can also completely compress a conduit having a comparatively large flow cross-section, the pressure applicators are fashioned such that, when the conduit is compressed, both pressure actuators actively press it together from both, opposite sides.

6 Claims, 4 Drawing Sheets

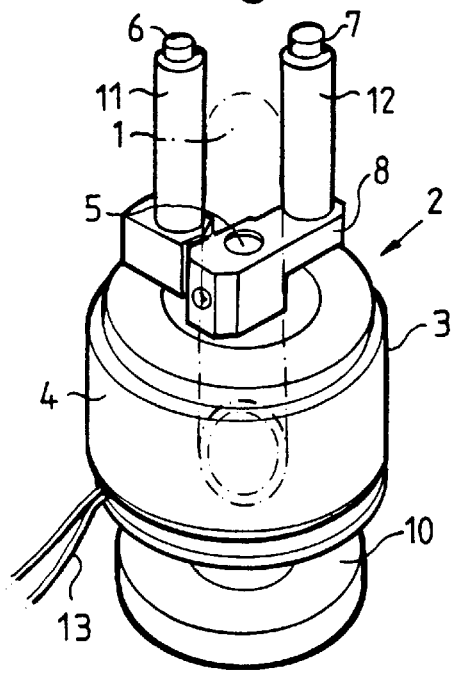
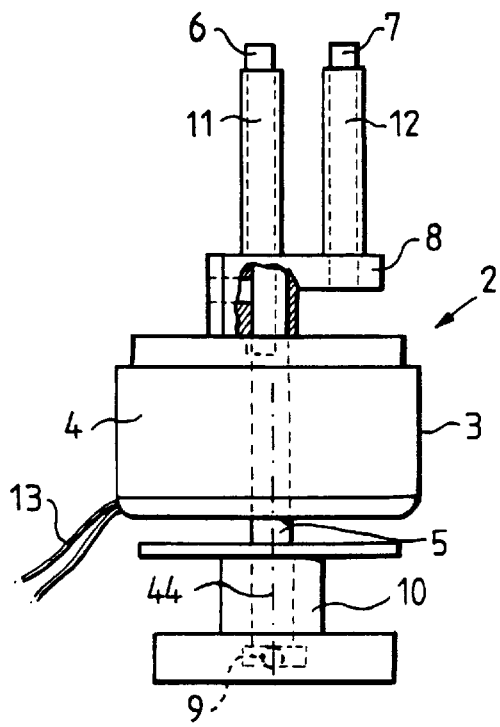
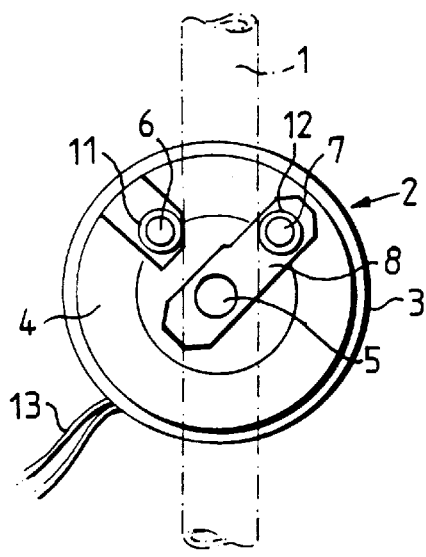
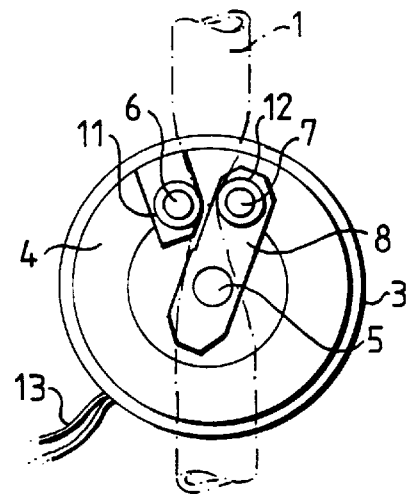

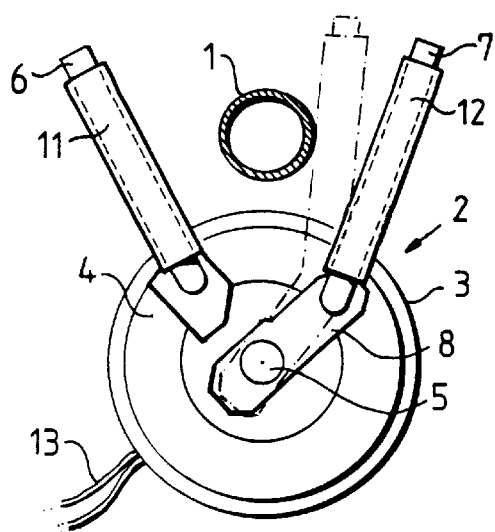
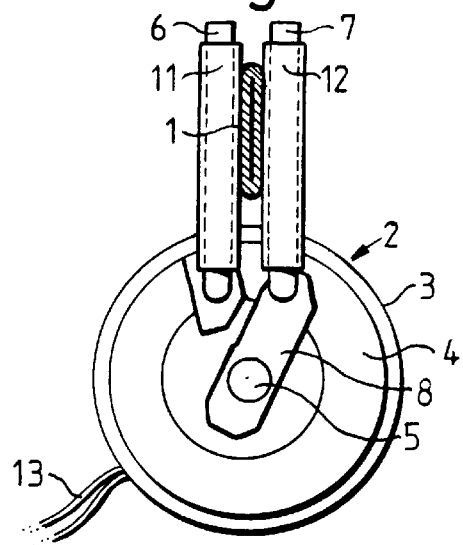
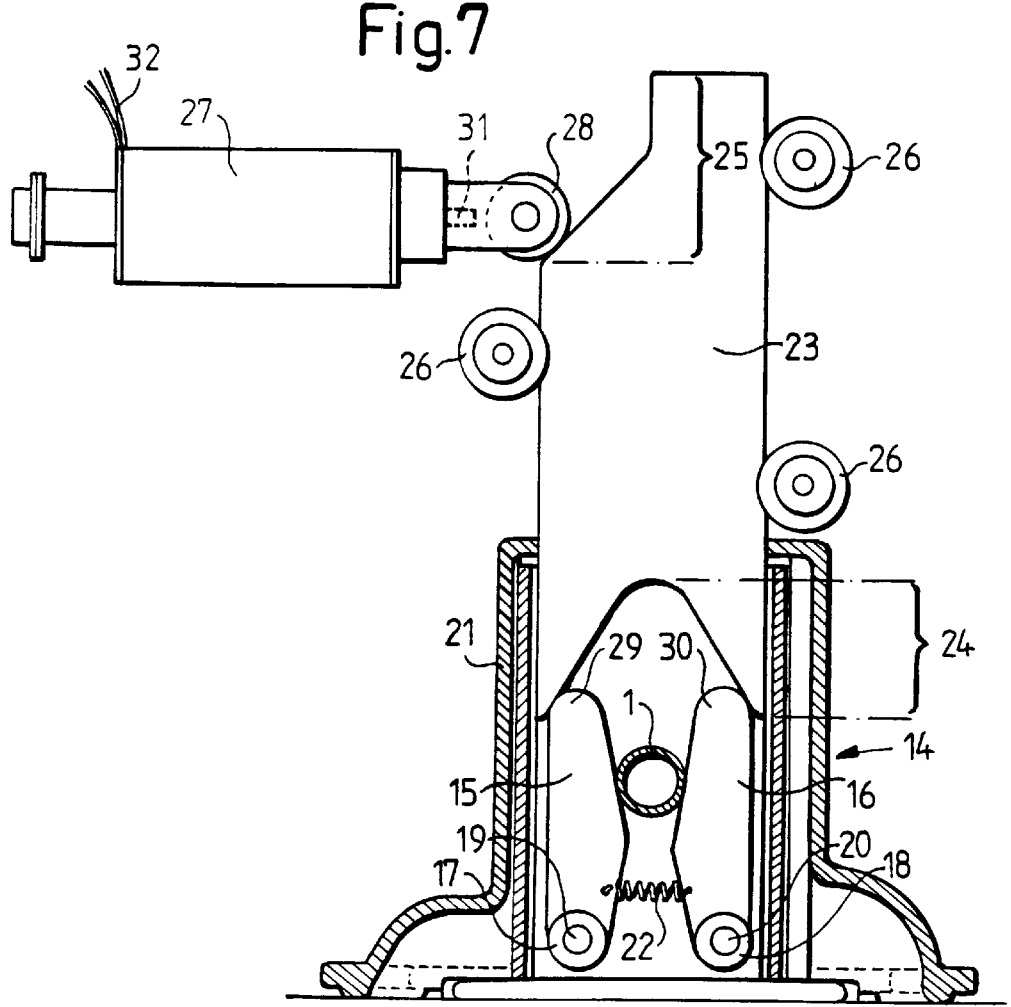

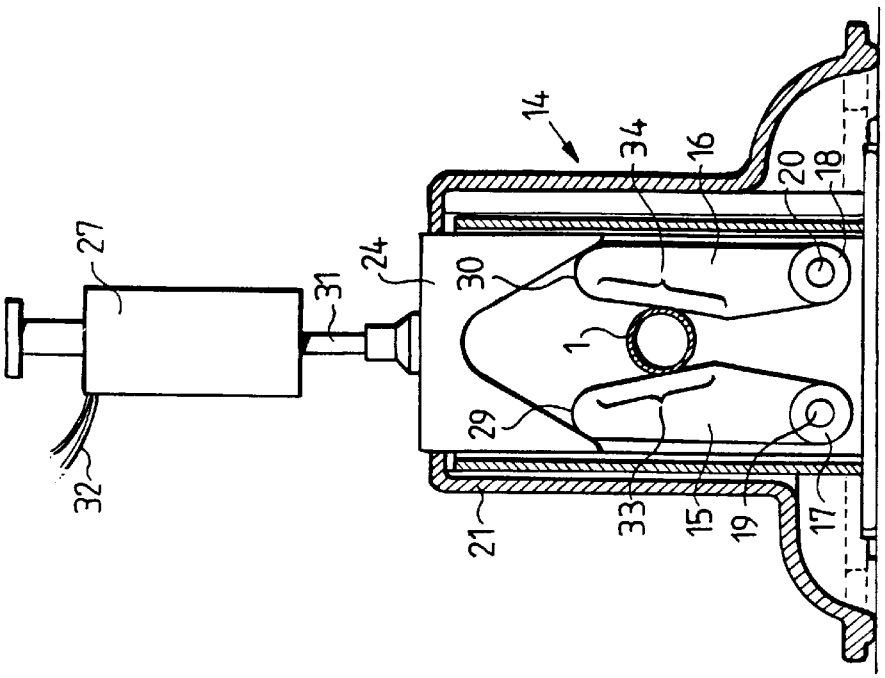
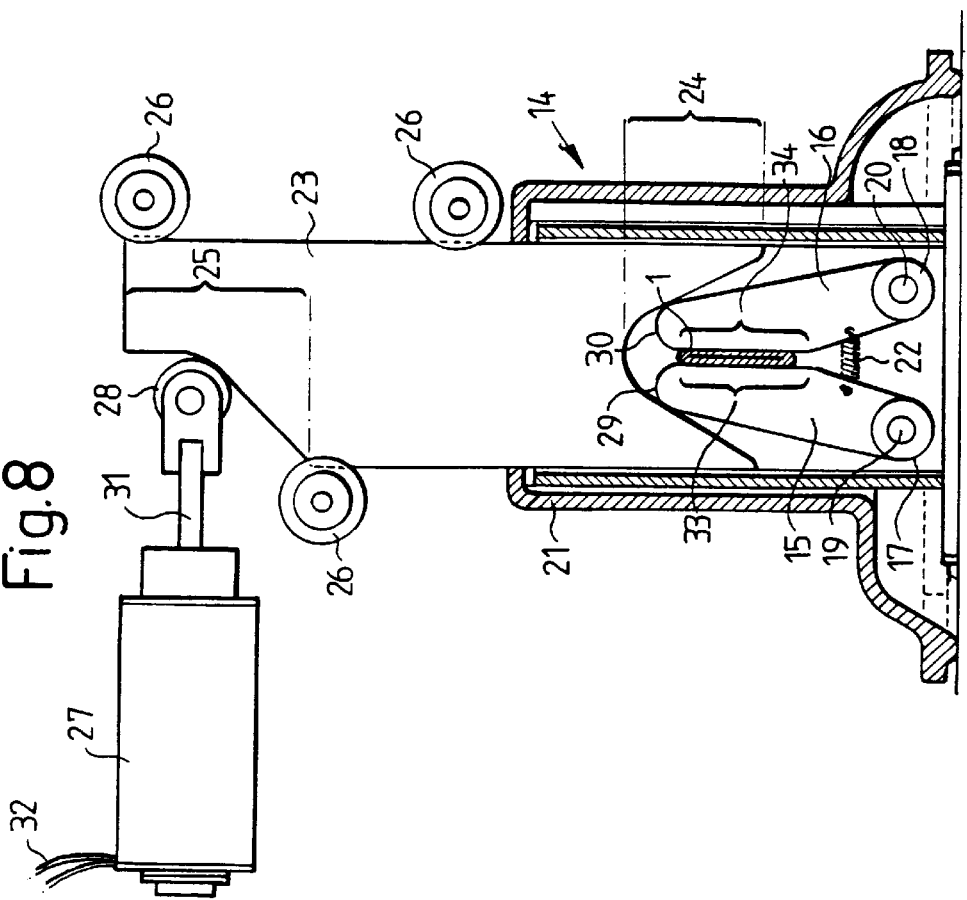

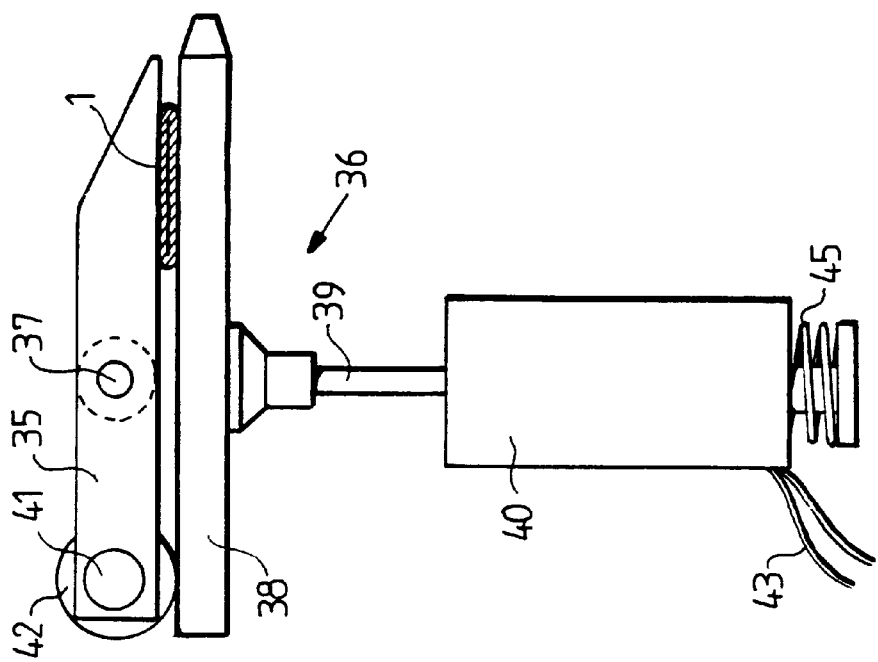
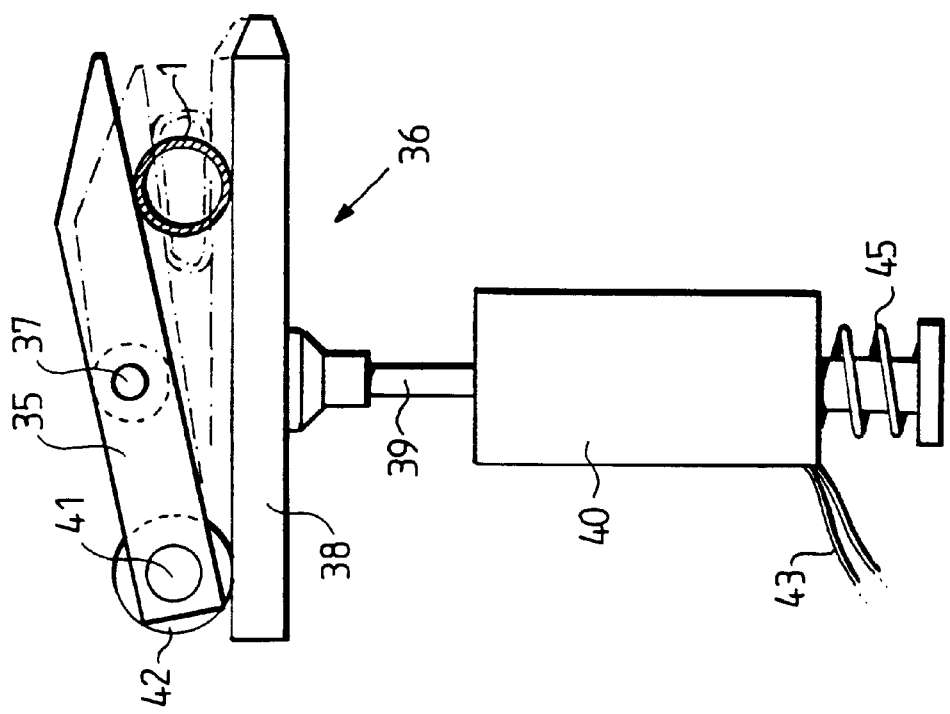

FLOW REGULATOR

BACKGROUND OF THE INVENTION

1. Field of the Invention

The invention is directed to a flow regulator, preferably in a respirator/ventilator, of the type having a compressible conduit through which a medium conduit flow is to be regulated flows and a choker valve arranged outside the conduit, the choker valve having pressure applicators arranged exactly opposite one another between which the conduit can be brought the pressure actuators leaving the flow cross-section of the conduit uninfluenced in a first limit position and pressing the conduit completely closed in a second limit position.

2. Description of the Prior Art

A flow regulator of this type is shown in the Siemens manual "Servo Ventilator 300" and is provided for regulating the gas flow through the expiration conduit of a respirator/ventilator during the exhalation phase. During an inspiration phase, the conduit is pressed completely together by one of the pressure applicators, which is attached to the end of a shaft of a solenoid, against the other pressure applicator, which is a fixed element. Since the movable pressure applicator constantly engages one side of the conduit, comparatively high wear arises at this side of the conduit. Further, the diameter of the expiration conduit, and thus the flow diameter as well, is made comparatively small at the clamping location compared to the rest of the conduit so that the choker valve can exert a force against the conduit so that it can be completely closed.

SUMMARY OF THE INVENTION

An object of the present invention is to provide a flow regulator of the type initially described, having a choker valve that is gentle on the conduit and that also can press a conduit with a comparatively large flow cross-section completely closed.

This object is inventively achieved in a flow regulator having pressure applicators on opposite sides of the conduit which are both moveable to actively press against the conduit from both sides when the cross-section of the conduit is to be modified. A more uniform distribution of the wear of the conduit is thereby established, yielding a comparatively long useful life.

Because the force when compressing the conduit can be distributed between the two pressure actuators, the expiration conduit can have a larger flow cross-section in that region wherein the choker valve operates compared to known conduits, without necessarily employing a choker valve that has a greater clamping force than known choker valves. Since the conduit can have a comparatively large flow cross-section, the respiratory resistance for the patient becomes lower.

In an embodiment of the inventive choker valve, the pressure applicators are fashioned such that they can compress the conduit in a manner producing an approximately symmetrical compression of the conduit. In this way, it is assured that a uniform distribution of the wear of the conduit is achieved in this region.

In another embodiment of the invention the choker valve has a rotary solenoid having a magnet housing and a shaft that is rotatable relative to the magnet housing, the magnet housing and the shaft each carrying a pressure applicator in the form of outwardly directly pegs. The pegs are arranged such that they move in opposed directions in a plane and between which a conduit can be located. The rotary solenoid is connected to a holder which is rotatable around a center axis, the center axis coinciding with the shaft of the rotary solenoid. A choker valve that is comparatively simple in structure and elegant at the same time is thereby established, with a symmetrical compression of the conduit being achieved.

A rotary solenoid of this type is shown and described in the handbook "Solenoids Design Manual" of Shindengen Electric Mfg. Co. Ltd.

In this embodiment of the choker valve of the invention, the pegs can proceed parallel to one another and to the shaft of the rotary solenoid, and one peg is connected to the shaft via an arm that proceeds perpendicularly to the shaft. That part of the expiration conduit that is to be pressed together proceeds perpendicularly to the shaft of the solenoid due to the longitudinal direction of the peg.

In a further version of this embodiment, the pegs can proceed perpendicularly against the shaft of the rotary solenoid.

In order to prevent the conduit from possibly being dislocated during compression because of the pegs, in accordance with the invention each peg is provided with a sleeve whose length approximately corresponds to the length of the peg, with the sleeves being freely rotatable around the pegs.

If the pegs proceed perpendicularly to the shaft of the rotary solenoid, the sleeves are axially displaceable on the pegs. This prevents the conduit from being dislocated in the longitudinal direction of the sleeves when being pressed together.

In a further embodiment of the choker valve of the invention, the choker valve has pressure applicators respectively formed by two arms arranged opposite one another, one end of each arm being pivotable around a respective fixed axis, and the arms are urged to swivel apart by a spring. The conduit is attachable between the arms, and the choker valve also has a part that is displaceable by a pressure actuator and which embraces the free ends of the arms so as to actuate them such that, in a first limit position of the part, the arms exhibit a spacing therebetween that at least corresponds to the outside diameter of the conduit and, in a second limit position, exhibit a spacing therebetween that corresponds to a completely compressed conduit. A choker valve that is very stable in structure and symmetrically compresses the conduit is thereby obtained.

In a version of the last-described choker valve of the invention, the displaceable part is V-shaped in profile and is displaceable in a longitudinal direction thereof by the pressure actuator. The longitudinal direction is the direction in which the free ends of the V-shaped part point. This allows the V-shaped part to embrace and actuate the free ends of the two arms.

In another version of this embodiment of the choker valve of the invention, the sides of the arms that are directed toward one another exhibit a shape so that at least the side sections that lie against the conduit in the second limit position proceed parallel to one another in this position. It is thereby assured that a uniform wear of the conduit is established.

The pressure actuator of this embodiment can be a solenoid conduit shaft can act on the displaceable part such that the part is displaced in its longitudinal direction.

Another version of this embodiment includes a cam plate having one end forming the V-shaped part and an opposite end fashioned wedge-like, and a solenoid whose shaft can act on a roller to press against the wedge-shaped part such that the cam plate with the V-shaped part is displaced in its longitudinal direction.

In another embodiment of the choker valve of the invention, a pressure applicator in the form of a first arm is rotatable around a first shaft, fixed in position, that proceeds perpendicularly to the longitudinal direction of the arm. The shaft is arranged approximately at the middle of the arm, and the choker valve also has another pressure applicator in the form of a second arm arranged so as to be displaceable against the rotatable pressure applicator by a second shaft by means of a pressure actuator. The second shaft is arranged perpendicularly to and exactly or approximately in front of the first shaft, so that the arms, in the region of their ends between which the conduit can be attached, exhibit a spacing therebetween in a first limit position of the second arm that at least corresponds to the outside diameter of the conduit, and exhibit a spacing in a second limit position that corresponds to a completely compressed conduit. As a result, a choker valve is established conduit pressure actuator can press the conduit together such that an approximately symmetrical compression ensues.

In a further version of the last-cited choker valve of the invention, in the region of their opposite ends (i.e. the ends which do not engage the conduit), the arms are provided with a spacer that separates the arms with a spacing that corresponds to a completely compressed conduit. As a result, it is assured that, given a conduit attached therebetween, the arms proceed parallel to one another in the second limit position with a spacing from one another that corresponds to a completely compressed conduit.

The aforementioned spacer can be a roller that is attached to the one or to the other arm. In this way, a barely noticeable friction between the spacer and the arm arises in the region of these ends, given a displacement of the second arm in the direction of the first arm.

The second shaft is preferably a solenoid shaft.

BRIEF DESCRIPTION OF THE DRAWINGS

FIG. 1 is a perspective view of a first embodiment of a flow regulator constructed in accordance with the principles of the present invention.

FIG. 2 is a side view, partly in section, of the flow regulator of FIG. 1.

FIGS. 3 and 4 are plan views of the flow regulator of FIGS. 1 and 2, respectively shown in the two limit positions.

FIGS. 5 and 6 are plan views of a second embodiment of a flow regulator according to the invention, respectively shown in the two limit positions.

FIGS. 7 and 8 are side views, each partly in section, of a third embodiment of a flow regulator according to the invention, respectively shown in the first and second limit positions.

FIG. 9 is a side view, partly in section, of a fourth embodiment of a flow regulator constructed in accordance with the invention.

FIGS. 10 and 11 are side views of a fourth embodiment of a flow regulator according to the invention, respectively showing the first and second limit positions.

DESCRIPTION OF THE PREFERRED EMBODIMENTS

FIG. 1 shows a perspective view of a one embodiment of a flow regulator of the invention, which is preferably employed in conjunction with a respirator/ventilator. The flow regulator includes an expiration conduit 1 through which an exhalation gas whose flow is to be regulated flows, the exhalation gas coming from a patient (not shown). The conduit 1 is shown with dot-dash lines in FIG. 1. The flow regulator also includes a choker valve 2 arranged outside the conduit 1. The choker valve 2 has a rotary solenoid 3 with a magnet housing 4 and a shaft 5 that is rotatable relative to the magnet housing 4. The magnet housing 4 is provided with a peg 6 that is arranged spaced from the shaft 5, and, via an arm 8 that proceeds perpendicularly to the shaft 5, the shaft 5 is connected to a further peg 7 that proceeds parallel to the peg 6 and that, due to the arm 8, exhibits the same spacing from the shaft 5 as the peg 7. The pegs 6 and 7, between which the conduit 1 is attachable, can each move in a common plane. In this exemplary embodiment, the pegs 6 and 7 proceed parallel to the shaft 5 of the rotary solenoid 3.

The rotary solenoid 3 is rotatably connected to a holder 10 via its shaft 5, which coincides with the center axis 44 of the rotary solenoid 3, and via a bearing 9. This is shown in FIG. 2, which shows a side view of the flow regulator. It is shown in FIGS. 1 and 2 that the peg are provided with respective sleeves 11 and 12 whose length approximately corresponds to the length of the pegs 6 and 7. The sleeves 11 and 12 are freely rotatable around the respective pegs 6 and 7.

It is shown in FIG. 1 and in FIG. 3, which is a plan view of the flow regulator, that, in a first limit position, the pegs 6 and 7 have a spacing from one another so that they leave the flow cross-section of the conduit 1 uninfluenced. By supplying the rotary solenoid 3 with more or less current via lines 13, the shaft 5 is turned relative to the magnet housing 4 so that the arm 8 and, at the same time, the peg 7, are rotated in the direction of the peg 6 of the magnet housing 4, causing the peg 7 to press against one side of the conduit 1. Since, as already described, the rotary solenoid 3 and the shaft 5 are rotatably arranged in a holder 10 and since the expiration conduit 1 is removably clamped to the respirator/ventilator, the magnet housing 4 turns in the direction of the peg 7, as does the peg 6 as well, so that the peg 6 presses against the other side of the conduit 1. As a result, the conduit 1 is pressed approximately symmetrically together, and the flow cross-section can now be varied such that a desired gas flow is obtained.

FIG. 4, which is a plan view of the flow regulator, shows that the rotary solenoid 3 is dimensioned such that the pegs 6 and 7 press the conduit 1 completely together in a second limit position. The above-described sleeves 11 and 12 of the pegs 6 and 7 prevent the conduit 1 from being dislocated while it is being pressed together. During an inspiration phase, the pegs 6 and 7 hold the conduit 1 in a compressed position. In a following exhalation phase, the power supply to the rotary solenoid 3 is turned off, so that the shaft 5 and the arm 8 and the peg 7 become powerless and return into their original position. Simultaneously therewith the magnet housing 4 and the peg 6 as well return into their original position, as shown in FIGS. 1 and 3.

FIGS. 5 and 6 show that the pegs 6 and 7 of the flow regulator, instead of proceeding parallel to the shaft 5 of the rotary solenoid 3, can be arranged such that they can proceed perpendicularly to the shaft 5. Otherwise, the flow regulator of FIGS. 5 and 6 is constructed in the same way and works in the way that was set forth in conjunction with FIG. 1. In such an embodiment, the expiration conduit 1 proceeds parallel to the shaft 5 of the rotary solenoid 3. FIG. 5 shows that—when power is supplied to the rotary solenoid 3—the shaft 5 is rotated relative to the magnet housing 4 so that the peg 7 lies against the outside wall of the conduit 1, as shown with the dot-dash version of the peg 7. Since the conduit 1, as already described, is removably secured to the respirator/ventilator, the outside wall of the conduit serves as a temporary detent for the peg 7. As a result, the magnet housing 4 together with the peg 6 are forced to move in the direction of the other side of the conduit 1 until it also lies against the conduit 1. An approximately symmetrical compression of the conduit 1 subsequently ensues until, as shown in FIG. 6, it is pressed completely together. The sleeves 11 and 12 are also axially displaceable on the pegs 6 and 7 so that conduit 1 is prevented from being dislocated in the longitudinal direction of the sleeves 11 and 12 in conjunction with a compression.

FIG. 7 shows a side view of another flow regulator version of the invention, wherein the choker valve 14 has a holder 21 shown in longitudinal section and two arms 15 and 16 arranged opposite one another in the holder 21 between which the conduit 1 is attachable. Respective ends 17 and 18 of the arms 15 and 16 are seated so as to be pivotable around respective shafts 19 and 20. The shafts 19 and 20 are in turn secured in the holder 21. With a spring element in the form, for example, of a compression spring 22, the arms 15 and 16 are urged to move apart. The choker valve 14 also has a cam plate 23 having one end composed of a V-shaped part 24 and another end 25 fashioned wedge-shaped. With supporting rollers 26 and with a solenoid 27, whose shaft 31 is provided with a pressure roller 28 that, as described in greater detail later, lies against the peripheral surface of the wedge-shaped part 25, the cam plate 23 is displaceable in its longitudinal direction so that the V-shaped part 25 can embrace the free ends 29 and 30 of the arms 15 and 16 in the holder 21 in one limit position. In this one limit position of the arms 15 and 16, the spacing between these arms is so large that, as shown in FIG. 7, it leaves the flow cross-section of the conduit 1 uninfluenced.

When power is supplied to the solenoid 27 via lines 32, the shaft 31 thereof actuates the pressure roller 28 such that it presses against the peripheral surface of the wedge-shaped part 25 of the cam plate 23, causing the V-shaped part 24 to be displaced in its longitudinal direction. The free ends 29 and 30 of the arms 15 and 16 are thereby actuated so that the arms 15 and 16 approach one another, causing the conduit 1 attached therebetween to be subjected to a symmetrical compression.

FIG. 8 shows a limit position in which the arms 15 and 16 have pressed the conduit 1 completely together. When the power supply to the solenoid 27 is switched off, the shaft 31 with its pressure roller becomes powerless, as a result whereof the compression spring 22 can pull the arms 15 and 16 apart. Due to the movement of the arms 15 and 16, the cam plates 23 is pushed back into its original position shown in FIG. 7. It can be clearly seen in FIG. 8 that the sides of the arms 15 and 16 directed toward one another exhibit such a shape that the side portions 33 and 34, which lies against the conduit 1 in this position, proceed parallel to one another.

FIG. 9 shows a further version of the flow regulator of the invention that has great similarity to the flow regulator described in conjunction with FIGS. 7 and 8. The difference is that the solenoid 27 is directly connected to the V-shaped part 24 via the shaft 31. When power is supplied to the solenoid 27 via lines 32, the shaft 31 is influenced to directly control the V-shaped part 24 such that the arms 15 and 16 are positioned in the described way and thus influence the flow crossection of the conduit 1.

FIGS. 10 and 11 show a further flow regulator of the invention wherein the choker valve has a first arm 35 that is preferably resiliently rotatable around a shaft 37 that is rigidly arranged in the respirator/ventilator (not shown). The shaft 9, which proceeds perpendicularly to the longitudinal direction of the arm 35, is attached at approximately the middle of the arm 35. The choker valve 36 also has a second arm 38 that can be displaced toward the first arm 35 with a second shaft 39 that is rigidly connected to the arm 38 and is arranged perpendicular to and exactly in front of the first shaft. In this exemplary embodiment, the shaft 39 is part of the solenoid 40. At one end, the arm 35 is provided with a roller 42 rotatable around a shaft 41, the peripheral surface of the roller 42 lying against the arm 38. The conduit 1 is attachable between the arms 35 and 38 in the region of their other ends. Here, the spacing between the arms 35 and 38 is dimensioned such that it at least corresponds to the outside diameter of the conduit. By supplying more or less power to the solenoid 40 via lines 43, the shaft 39 of the solenoid 40 is influenced to press the arm 38 against the roller 42 such that the arm 38 is turned around its shaft. As a result, the spacing between the arms 35 and 37 is reduced in the region of their other ends where the conduit 1 is attached, causing the conduit 1 to be compressed simultaneously from two opposite sides. The dot-dash lines of the arms 35 and 37 and of the conduit 1 are intended to show such a compression of the conduit 1.

FIG. 11 shows that the arm 38, with the assistance of the shaft 39 of the solenoid 40, has influenced the roller 42 to turn the arm 35 into a limit position in which the arms 35 and 38 proceed parallel to one another and in which the conduit 1 is pressed completely together. The parallelism of the arms 35 and 38 is achieved because the roller 42 is made so large that it separates the arms 35 and 38 from one another with a spacing that corresponds to a completely compressed conduit. As was already described, the solenoid 40 now holds the conduit 1 in a compressed position during an inhalation phase. During a following exhalation phase, the power supply to the solenoid 40 is switched off, so that its shaft 39 becomes powerless. A compression spring 45 causes the shaft 39, and thus the arm 38 as well, to be pushed back into the original position shown in FIG. 10. As already set forth, the arms 35 and 38 of this flow regulator also exhibit a motion pattern so that an approximately symmetrical compression of the conduit 1 is achieved.

The common feature of all embodiments of the invention is that the pressure applicators in the form of pegs or arms are fashioned such that, when pressing the expiration conduit 1 together, they can actively compress the conduit 1 from both sides such that an approximately symmetrical pressing is established. As a result, a choker valve is obtained that is comparatively gentle on the conduit. Since the force required for pressing the conduit completely together is distributed between two pressure applicators attached opposite one another, a conduit having a comparatively large flow cross-section can be employed without using a choker valve that exhibits a larger clamping force than known choker valves.

Although modifications and changes may be suggested by those skilled in the art, it is the intention of the inventors to embody within the patent warranted hereon all changes and modifications as reasonably and properly come within the scope of their contribution to the art.

We claim as our invention:
1. A flow regulator comprising:
   a conduit having a flowing medium therein which is to be regulated as to flow;
   a choker valve disposed at an exterior of said conduit for modifying a cross-section of said conduit for regulating said flow;

said choker valve comprising first and second pegs disposed on opposite sides of said conduit, and a rotary solenoid having a housing and a shaft rotatable relative to said housing, said first peg being attached to said housing and said second peg being attached to said shaft, said first and second pegs being movable in a common plane by said rotary solenoid with said conduit therebetween, between a first limit position wherein said cross-section of said conduit is unaltered and a second limit position wherein said conduit is completely compressed and said flow is completely restricted; and a holder having a center axis around which said rotary solenoid is rotatable, said center axis coinciding with a center axis of said shaft of said rotary solenoid.

2. A flow regulator as claimed in claim 1 wherein said first and second pegs are respectively mounted on said housing and on said shaft for symmetrically compressing said conduit between said first and second limit positions.

3. A flow regulator as claimed in claim 1 wherein said first and second pegs are disposed parallel to each other and to said shaft of said rotary solenoid, and further comprising a shaft arm connected to and extending substantially perpendicular to said shaft, on which said second peg is attached.

4. A flow regulator as claimed in claim 1 wherein said pegs are disposed parallel to each other and perpendicular to said shaft of said rotary solenoid, and further comprising a shaft arm connected to and extending substantially perpendicular to said shaft, on which said second peg is attached.

5. A flow regulator as claimed in claim 1 wherein each of said first and second pegs has a length and wherein said flow regulator further comprises a first sleeve disposed on and freely rotatable around said first peg and a second sleeve disposed on and freely rotatable around said second peg, said first and second sleeves each having a length substantially equal to the length of said first and second pegs.

6. A flow regulator as claimed in claim 5 wherein said first and second sleeves are axially displaceable respectively on said first and second pegs.

\* \* \* \* \*